United States Patent
Sasaki et al.

(10) Patent No.: US 10,619,216 B2
(45) Date of Patent: Apr. 14, 2020

(54) METHOD FOR DETECTING RP2-ARHGAP6 GENE

(71) Applicants: Astellas Pharma Inc., Tokyo (JP); National Cancer Center, Tokyo (JP)

(72) Inventors: Hiroki Sasaki, Tokyo (JP); Hitoshi Ichikawa, Tokyo (JP)

(73) Assignees: Astellas Pharma Inc., Tokyo (JP); National Cancer Center, Tokyo (JP)

( * ) Notice: Subject to any disclaimer, the term of this patent is extended or adjusted under 35 U.S.C. 154(b) by 19 days.

(21) Appl. No.: 15/753,994

(22) PCT Filed: Aug. 23, 2016

(86) PCT No.: PCT/JP2016/074442
§ 371 (c)(1),
(2) Date: Mar. 1, 2018

(87) PCT Pub. No.: WO2017/033906
PCT Pub. Date: Mar. 2, 2017

(65) Prior Publication Data
US 2018/0251850 A1 Sep. 6, 2018

Related U.S. Application Data

(60) Provisional application No. 62/209,130, filed on Aug. 24, 2015.

(30) Foreign Application Priority Data

Dec. 21, 2015 (JP) ................................. 2015-248292

(51) Int. Cl.
| | | |
|---|---|---|
| C12Q 1/68 | (2018.01) | |
| C12Q 1/6886 | (2018.01) | |
| C12N 15/09 | (2006.01) | |
| C12Q 1/6853 | (2018.01) | |
| C12Q 1/686 | (2018.01) | |

(52) U.S. Cl.
CPC .......... *C12Q 1/6886* (2013.01); *C12N 15/09* (2013.01); *C12Q 1/68* (2013.01); *C12Q 1/686* (2013.01); *C12Q 1/6853* (2013.01); *C12Q 2600/106* (2013.01); *C12Q 2600/118* (2013.01); *C12Q 2600/156* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

2012/0258998 A1* 10/2012 Tan ..................... A61K 31/7088
514/44 A

FOREIGN PATENT DOCUMENTS

| WO | WO2005/002414 A2 | 1/2005 |
| WO | WO2012/139134 A2 | 10/2012 |
| WO | WO2015/142293 A1 | 9/2015 |

OTHER PUBLICATIONS

New England Biolabs 1996/1997 catalog; p. 111 (Year: 1997).*
Wang et al. Nature Genetics, vol. 43, No. 12, pp. 1219-1223, including online methods (Year: 2011).*
Extended European Search Report for EP Application No. 16839253.8, dated Mar. 13, 2019.
International Search Report for PCT/JP2016/07442 dated Oct. 11, 2016 (Oct. 11, 2016).
Borkhardt, A et al, The human GRAF gene is fused to MLL in a unique t(5;11)(q31;q23) et al, Proc. Natl. Acad.Sci. USA, 2000, vol. 97, No. 16, pp. 9168-9173, Summary.
Panagopoulos I et al, MLL/GRAF fusion in an infant (AML M5b) with a cytogenetically cryptic ins (5;11)(q31;q23q23), Genes Chromosomes Cancer,2004, vol. 41, No. 4, pp. 400-404,sum.
Yao F et al, Recurrent Fusion Genes in Gastric Cancer: CLDN18-ARHGAP26 Induces Loss of Epithelial Integrity, Cell Rep, Jul. 2015, vol. 12, No. 2, pp. 272-285, Summary.
Veltel S et al, The retinitis pigmentosa 2 gene product is a GTPase-activating protein for Arf-like 3., Nat. Struct. Mol.Biol., 2008, vol. 15, No. 4, pp. 373-380 abstract.
Cancer Genome Atlas Research Network, Comprehensive molecular characterization of gastric adenocarcinoma, Nature, 2014, vol. 513, No. 7517, pp. 202-209, Fig 4.

* cited by examiner

*Primary Examiner* — Juliet C Switzer

(57) ABSTRACT

The object of the invention is to elucidate a new causative gene of cancer, polynucleotide, and thereby provide a method for detecting the polynucleotide or a polypeptide that is encoded by the polynucleotide, as well as a primer set or a detection kit for such detection. The detection method detects a fusion gene of a part of an RP2 gene and a part of an ARHGAP6 gene, or a fusion protein encoded by such gene. The primer set includes a sense primer designed from a section encoding RP2 and an antisense primer designed from a section encoding ARHGAP6.

5 Claims, 1 Drawing Sheet
Specification includes a Sequence Listing.

SEQUENCE LISTING

```
<160> NUMBER OF SEQ ID NOS: 10

<210> SEQ ID NO 1
<211> LENGTH: 2439
<212> TYPE: DNA
<213> ORGANISM: Homo sapiens
<220> FEATURE:
<221> NAME/KEY: CDS
<222> LOCATION: (1)..(2439)

<400> SEQUENCE: 1 atg ggc tgc ttc ttc tcc aag aga cgg aag gct gac aag gag tcg cgg      48
Met Gly Cys Phe Phe Ser Lys Arg Arg Lys Ala Asp Lys Glu Ser Arg
1               5                   10                  15 ccc gag aac gag gag gag cgg cca aag cag tac agc tgg gat cag cgc      96
Pro Glu Asn Glu Glu Glu Arg Pro Lys Gln Tyr Ser Trp Asp Gln Arg
                20                  25                  30 gag aag ggt gat ttc acc tgg aac agc atg tca ggc cgc agt gta cgg     144
Glu Lys Gly Asp Phe Thr Trp Asn Ser Met Ser Gly Arg Ser Val Arg
            35                  40                  45 ctg agg tca gtc ccc atc cag agt ctc tca gag ctg gag agg gcc cgg     192
Leu Arg Ser Val Pro Ile Gln Ser Leu Ser Glu Leu Glu Arg Ala Arg
        50                  55                  60 ctg cag gaa gtg gct ttt tat cag ttg caa cag gac tgt gac ctg agc     240
Leu Gln Glu Val Ala Phe Tyr Gln Leu Gln Gln Asp Cys Asp Leu Ser
65                  70                  75                  80 tgt cag atc acc att ccc aaa gat gga caa aag aga aag aaa tct tta     288
Cys Gln Ile Thr Ile Pro Lys Asp Gly Gln Lys Arg Lys Lys Ser Leu
                85                  90                  95 aga aag aaa ctg gat tca cta gga aag gag aaa aac aaa gac aaa gaa     336
Arg Lys Lys Leu Asp Ser Leu Gly Lys Glu Lys Asn Lys Asp Lys Glu
                100                 105                 110 ttc atc cca cag gca ttt gga atg ccc tta tcc caa gtc att gcg aat     384
Phe Ile Pro Gln Ala Phe Gly Met Pro Leu Ser Gln Val Ile Ala Asn
            115                 120                 125 gac agg gcc tat aaa ctc aag cag gac ttg cag agg gac gag cag aaa     432
Asp Arg Ala Tyr Lys Leu Lys Gln Asp Leu Gln Arg Asp Glu Gln Lys
        130                 135                 140 gat gca tct gac ttt gtg gct tcc ctc ctc cca ttt gga aat aaa aga     480
Asp Ala Ser Asp Phe Val Ala Ser Leu Leu Pro Phe Gly Asn Lys Arg
145                 150                 155                 160 caa aac aaa gaa ctc tca agc agt aac tca tct ctc agc tca acc tca     528
Gln Asn Lys Glu Leu Ser Ser Ser Asn Ser Ser Leu Ser Ser Thr Ser
                165                 170                 175 gaa aca ccg aat gag tca acg tcc cca aac acc ccg gaa ccg gct cct     576
Glu Thr Pro Asn Glu Ser Thr Ser Pro Asn Thr Pro Glu Pro Ala Pro
            180                 185                 190 cgg gct agg agg agg ggt gcc atg tca gtg gat tct atc acc gat ctt     624
```

```
                Arg Ala Arg Arg Arg Gly Ala Met Ser Val Asp Ser Ile Thr Asp Leu
                            195                 200                 205 gat gac aat cag tct cga cta cta gaa gct tta caa ctt tcc ttg cct          672
Asp Asp Asn Gln Ser Arg Leu Leu Glu Ala Leu Gln Leu Ser Leu Pro
210                 215                 220 gct gag gct caa agt aaa aag gaa aaa gcc aga gat aag aaa ctc agt          720
Ala Glu Ala Gln Ser Lys Lys Glu Lys Ala Arg Asp Lys Lys Leu Ser
225                 230                 235                 240 ctg aat cct att tac aga cag gtc cct agg ctg gtg gac agc tgc tgt          768
Leu Asn Pro Ile Tyr Arg Gln Val Pro Arg Leu Val Asp Ser Cys Cys
                    245                 250                 255 cag cac cta gaa aaa cat ggc ctc cag aca gtg ggg ata ttc cga gtt          816
Gln His Leu Glu Lys His Gly Leu Gln Thr Val Gly Ile Phe Arg Val
                260                 265                 270 gga agc tca aaa aag aga gtg aga caa tta cgt gag gaa ttt gac cgt          864
Gly Ser Ser Lys Lys Arg Val Arg Gln Leu Arg Glu Glu Phe Asp Arg
            275                 280                 285 ggg att gat gtc tct ctg gag gag gag cac agt gtt cat gat gtg gca          912
Gly Ile Asp Val Ser Leu Glu Glu Glu His Ser Val His Asp Val Ala
290                 295                 300 gcc ttg ctg aaa gag ttc ctg agg gac atg cca gac ccc ctt ctc acc          960
Ala Leu Leu Lys Glu Phe Leu Arg Asp Met Pro Asp Pro Leu Leu Thr
305                 310                 315                 320 agg gag ctg tac aca gct ttc atc aac act ctc ttg ttg gag ccg gag         1008
Arg Glu Leu Tyr Thr Ala Phe Ile Asn Thr Leu Leu Leu Glu Pro Glu
                    325                 330                 335 gaa cag ctg ggc acc ttg cag ctc ctc ata tac ctt cta cct ccc tgc         1056
Glu Gln Leu Gly Thr Leu Gln Leu Leu Ile Tyr Leu Leu Pro Pro Cys
                340                 345                 350 aac tgc gac acc ctc cac cgc ctg cta cag ttc ctc tcc atc gtg gcc         1104
Asn Cys Asp Thr Leu His Arg Leu Leu Gln Phe Leu Ser Ile Val Ala
            355                 360                 365 agg cat gcc gat gac aac atc agc aaa gat ggg caa gag gtc act ggg         1152
Arg His Ala Asp Asp Asn Ile Ser Lys Asp Gly Gln Glu Val Thr Gly
370                 375                 380 aat aaa atg aca tct cta aac tta gcc acc ata ttt gga ccc aac ctg         1200
Asn Lys Met Thr Ser Leu Asn Leu Ala Thr Ile Phe Gly Pro Asn Leu
385                 390                 395                 400 ctg cac aag cag aag tca tca gac aaa gaa ttc tca gtt cag agt tca         1248
Leu His Lys Gln Lys Ser Ser Asp Lys Glu Phe Ser Val Gln Ser Ser
                    405                 410                 415 gcc cgg gct gag gag agc acg gcc atc atc gct gtt gtg caa aag atg         1296
Ala Arg Ala Glu Glu Ser Thr Ala Ile Ile Ala Val Val Gln Lys Met
                420                 425                 430 att gaa aat tat gaa gcc ctg ttc atg gtt ccc cca gat ctc cag aac         1344
Ile Glu Asn Tyr Glu Ala Leu Phe Met Val Pro Pro Asp Leu Gln Asn
            435                 440                 445 gaa gtg ctg atc agc ctg tta gag acc gat cct gat gtc gtg gac tat         1392
Glu Val Leu Ile Ser Leu Leu Glu Thr Asp Pro Asp Val Val Asp Tyr
450                 455                 460 tta ctc aga aga aag gct tcc caa tca tca agc cct gac atg ctg cag         1440
Leu Leu Arg Arg Lys Ala Ser Gln Ser Ser Ser Pro Asp Met Leu Gln
465                 470                 475                 480 tcg gaa gtt tcc ttt tcc gtg gga ggg agg cat tca tct aca gac tcc         1488
Ser Glu Val Ser Phe Ser Val Gly Gly Arg His Ser Ser Thr Asp Ser
                    485                 490                 495 aac aag gcc tcc agc gga gac atc tcc cct tat gac aac aac tcc cca         1536
Asn Lys Ala Ser Ser Gly Asp Ile Ser Pro Tyr Asp Asn Asn Ser Pro
                500                 505                 510
```

-continued

| | | |
|---|---|---|
| gtg ctg tct gag cgc tcc ctg ctg gct atg caa gag gac gcg gcc ccg<br>Val Leu Ser Glu Arg Ser Leu Leu Ala Met Gln Glu Asp Ala Ala Pro<br>     515                  520                  525 | 1584 |
| ggg ggc tcg gag aag ctt tac aga gtg cca ggg cag ttt atg ctg gtg<br>Gly Gly Ser Glu Lys Leu Tyr Arg Val Pro Gly Gln Phe Met Leu Val<br>530                    535                  540 | 1632 |
| ggc cac ttg tcg tcg tca aag tca agg gaa agt tct cct gga cca agg<br>Gly His Leu Ser Ser Ser Lys Ser Arg Glu Ser Ser Pro Gly Pro Arg<br>545                    550                  555                  560 | 1680 |
| ctt ggg aaa gat ctg tca gag gag cct ttc gat atc tgg gga act tgg<br>Leu Gly Lys Asp Leu Ser Glu Glu Pro Phe Asp Ile Trp Gly Thr Trp<br>                  565                  570                  575 | 1728 |
| cat tca aca tta aaa agc gga tcc aaa gac cca gga atg aca ggt tcc<br>His Ser Thr Leu Lys Ser Gly Ser Lys Asp Pro Gly Met Thr Gly Ser<br>                      580                  585                  590 | 1776 |
| tct gga gac att ttt gaa agc agc tcc cta aga gcg ggg ccc tgc tcc<br>Ser Gly Asp Ile Phe Glu Ser Ser Ser Leu Arg Ala Gly Pro Cys Ser<br>              595                  600                  605 | 1824 |
| ctt tct caa ggg aac ctg tcc cca aat tgg cct cgg tgg cag ggg agc<br>Leu Ser Gln Gly Asn Leu Ser Pro Asn Trp Pro Arg Trp Gln Gly Ser<br>610                    615                  620 | 1872 |
| ccc gca gag ctg gac agc gac acg cag ggg gct cgg agg act cag gcc<br>Pro Ala Glu Leu Asp Ser Asp Thr Gln Gly Ala Arg Arg Thr Gln Ala<br>625                    630                  635                  640 | 1920 |
| gca gcc ccc gcg acg gag ggc agg gcc cac cct gcg gtg tcg cgc gcc<br>Ala Ala Pro Ala Thr Glu Gly Arg Ala His Pro Ala Val Ser Arg Ala<br>                      645                  650                  655 | 1968 |
| tgc agc acg ccc cac gtc cag gtg gca ggg aaa gcc gag cgg ccc acg<br>Cys Ser Thr Pro His Val Gln Val Ala Gly Lys Ala Glu Arg Pro Thr<br>                        660                  665                  670 | 2016 |
| gcc agg tcg gag cag tac ttg acc ctg agc ggc gcc cac gac ctc agc<br>Ala Arg Ser Glu Gln Tyr Leu Thr Leu Ser Gly Ala His Asp Leu Ser<br>                  675                  680                  685 | 2064 |
| gag agt gag ctg gat gtg gcc ggg ctg cag agc cgg gcc aca cct cag<br>Glu Ser Glu Leu Asp Val Ala Gly Leu Gln Ser Arg Ala Thr Pro Gln<br>690                    695                  700 | 2112 |
| tgc caa aga ccc cat ggg agt ggg agg gat gac aag cgg ccc ccg cct<br>Cys Gln Arg Pro His Gly Ser Gly Arg Asp Asp Lys Arg Pro Pro Pro<br>705                    710                  715                  720 | 2160 |
| cca tac ccg ggc cca ggg aag ccc gcg gca gcg gca gcc tgg atc cag<br>Pro Tyr Pro Gly Pro Gly Lys Pro Ala Ala Ala Ala Ala Trp Ile Gln<br>                      725                  730                  735 | 2208 |
| ggg ccc ccg gaa ggc gtg gag aca ccc acg gac cag gga ggc caa gca<br>Gly Pro Pro Glu Gly Val Glu Thr Pro Thr Asp Gln Gly Gly Gln Ala<br>                        740                  745                  750 | 2256 |
| gcc gag cga gag cag cag gtc acg cag aaa aaa ctg agc agc gcc aac<br>Ala Glu Arg Glu Gln Gln Val Thr Gln Lys Lys Leu Ser Ser Ala Asn<br>                755                  760                  765 | 2304 |
| tcc ctg cca gcg ggc gag cag gac agt ccg cgc ctg ggg gac gct ggc<br>Ser Leu Pro Ala Gly Glu Gln Asp Ser Pro Arg Leu Gly Asp Ala Gly<br>770                    775                  780 | 2352 |
| tgg ctc gac tgg cag aga gag cgc tgg cag atc tgg gag ctc ctg tcg<br>Trp Leu Asp Trp Gln Arg Glu Arg Trp Gln Ile Trp Glu Leu Leu Ser<br>785                    790                  795                  800 | 2400 |
| acc gac aac ccc gat gcc ctg ccc gag acg ctg gtc tga<br>Thr Asp Asn Pro Asp Ala Leu Pro Glu Thr Leu Val<br>                    805                  810 | 2439 |

<210> SEQ ID NO 2
<211> LENGTH: 812

<212> TYPE: PRT
<213> ORGANISM: Homo sapiens

<400> SEQUENCE: 2

```
Met Gly Cys Phe Phe Ser Lys Arg Arg Lys Ala Asp Lys Glu Ser Arg
1               5                   10                  15

Pro Glu Asn Glu Glu Arg Pro Lys Gln Tyr Ser Trp Asp Gln Arg
            20                  25                  30

Glu Lys Gly Asp Phe Thr Trp Asn Ser Met Ser Gly Arg Ser Val Arg
            35                  40                  45

Leu Arg Ser Val Pro Ile Gln Ser Leu Ser Glu Leu Glu Arg Ala Arg
50                  55                  60

Leu Gln Glu Val Ala Phe Tyr Gln Leu Gln Gln Asp Cys Asp Leu Ser
65                  70                  75                  80

Cys Gln Ile Thr Ile Pro Lys Asp Gly Gln Lys Arg Lys Lys Ser Leu
                85                  90                  95

Arg Lys Lys Leu Asp Ser Leu Gly Lys Glu Asn Lys Asp Lys Glu
            100                 105                 110

Phe Ile Pro Gln Ala Phe Gly Met Pro Leu Ser Gln Val Ile Ala Asn
            115                 120                 125

Asp Arg Ala Tyr Lys Leu Lys Gln Asp Leu Gln Arg Asp Glu Gln Lys
130                 135                 140

Asp Ala Ser Asp Phe Val Ala Ser Leu Leu Pro Phe Gly Asn Lys Arg
145                 150                 155                 160

Gln Asn Lys Glu Leu Ser Ser Ser Asn Ser Ser Leu Ser Ser Thr Ser
                165                 170                 175

Glu Thr Pro Asn Glu Ser Thr Ser Pro Asn Thr Pro Glu Pro Ala Pro
            180                 185                 190

Arg Ala Arg Arg Arg Gly Ala Met Ser Val Asp Ser Ile Thr Asp Leu
            195                 200                 205

Asp Asp Asn Gln Ser Arg Leu Leu Glu Ala Leu Gln Leu Ser Leu Pro
210                 215                 220

Ala Glu Ala Gln Ser Lys Lys Glu Lys Ala Arg Asp Lys Lys Leu Ser
225                 230                 235                 240

Leu Asn Pro Ile Tyr Arg Gln Val Pro Arg Leu Val Asp Ser Cys Cys
                245                 250                 255

Gln His Leu Glu Lys His Gly Leu Gln Thr Val Gly Ile Phe Arg Val
            260                 265                 270

Gly Ser Ser Lys Lys Arg Val Arg Gln Leu Arg Glu Glu Phe Asp Arg
            275                 280                 285

Gly Ile Asp Val Ser Leu Glu Glu His Ser Val His Asp Val Ala
290                 295                 300

Ala Leu Leu Lys Glu Phe Leu Arg Asp Met Pro Asp Pro Leu Leu Thr
305                 310                 315                 320

Arg Glu Leu Tyr Thr Ala Phe Ile Asn Thr Leu Leu Leu Glu Pro Glu
                325                 330                 335

Glu Gln Leu Gly Thr Leu Gln Leu Leu Ile Tyr Leu Leu Pro Pro Cys
            340                 345                 350

Asn Cys Asp Thr Leu His Arg Leu Leu Gln Phe Leu Ser Ile Val Ala
            355                 360                 365

Arg His Ala Asp Asp Asn Ile Ser Lys Asp Gly Gln Glu Val Thr Gly
370                 375                 380

Asn Lys Met Thr Ser Leu Asn Leu Ala Thr Ile Phe Gly Pro Asn Leu
385                 390                 395                 400
```

```
Leu His Lys Gln Lys Ser Ser Asp Lys Glu Phe Ser Val Gln Ser Ser
            405                 410                 415

Ala Arg Ala Glu Glu Ser Thr Ala Ile Ile Ala Val Val Gln Lys Met
            420                 425                 430

Ile Glu Asn Tyr Glu Ala Leu Phe Met Val Pro Pro Asp Leu Gln Asn
            435                 440                 445

Glu Val Leu Ile Ser Leu Leu Glu Thr Asp Pro Asp Val Val Asp Tyr
            450                 455                 460

Leu Leu Arg Arg Lys Ala Ser Gln Ser Ser Ser Pro Asp Met Leu Gln
465                 470                 475                 480

Ser Glu Val Ser Phe Ser Val Gly Gly Arg His Ser Ser Thr Asp Ser
                485                 490                 495

Asn Lys Ala Ser Ser Gly Asp Ile Ser Pro Tyr Asp Asn Asn Ser Pro
                500                 505                 510

Val Leu Ser Glu Arg Ser Leu Leu Ala Met Gln Glu Asp Ala Ala Pro
            515                 520                 525

Gly Gly Ser Glu Lys Leu Tyr Arg Val Pro Gly Gln Phe Met Leu Val
            530                 535                 540

Gly His Leu Ser Ser Ser Lys Ser Arg Glu Ser Ser Pro Gly Pro Arg
545                 550                 555                 560

Leu Gly Lys Asp Leu Ser Glu Glu Pro Phe Asp Ile Trp Gly Thr Trp
                565                 570                 575

His Ser Thr Leu Lys Ser Gly Ser Lys Asp Pro Gly Met Thr Gly Ser
                580                 585                 590

Ser Gly Asp Ile Phe Glu Ser Ser Leu Arg Ala Gly Pro Cys Ser
                595                 600                 605

Leu Ser Gln Gly Asn Leu Ser Pro Asn Trp Pro Arg Trp Gln Gly Ser
            610                 615                 620

Pro Ala Glu Leu Asp Ser Asp Thr Gln Gly Ala Arg Arg Thr Gln Ala
625                 630                 635                 640

Ala Ala Pro Ala Thr Glu Gly Arg Ala His Pro Ala Val Ser Arg Ala
                645                 650                 655

Cys Ser Thr Pro His Val Gln Val Ala Gly Lys Ala Glu Arg Pro Thr
                660                 665                 670

Ala Arg Ser Glu Gln Tyr Leu Thr Leu Ser Gly Ala His Asp Leu Ser
            675                 680                 685

Glu Ser Glu Leu Asp Val Ala Gly Leu Gln Ser Arg Ala Thr Pro Gln
            690                 695                 700

Cys Gln Arg Pro His Gly Ser Gly Arg Asp Asp Lys Arg Pro Pro Pro
705                 710                 715                 720

Pro Tyr Pro Gly Pro Gly Lys Pro Ala Ala Ala Ala Trp Ile Gln
                725                 730                 735

Gly Pro Pro Glu Gly Val Glu Thr Pro Thr Asp Gln Gly Gly Gln Ala
            740                 745                 750

Ala Glu Arg Glu Gln Gln Val Thr Gln Lys Lys Leu Ser Ser Ala Asn
            755                 760                 765

Ser Leu Pro Ala Gly Glu Gln Asp Ser Pro Arg Leu Gly Asp Ala Gly
            770                 775                 780

Trp Leu Asp Trp Gln Arg Glu Arg Trp Gln Ile Trp Glu Leu Leu Ser
785                 790                 795                 800

Thr Asp Asn Pro Asp Ala Leu Pro Glu Thr Leu Val
                805                 810
```

```
<210> SEQ ID NO 3
<211> LENGTH: 18
<212> TYPE: DNA
<213> ORGANISM: Homo sapiens

<400> SEQUENCE: 3
caaactaagg ctgcggac                                                 18

<210> SEQ ID NO 4
<211> LENGTH: 18
<212> TYPE: DNA
<213> ORGANISM: Homo sapiens

<400> SEQUENCE: 4
gtgctctacc tctgtagg                                                 18

<210> SEQ ID NO 5
<211> LENGTH: 18
<212> TYPE: DNA
<213> ORGANISM: Homo sapiens

<400> SEQUENCE: 5
gttcacgcca cactctag                                                 18

<210> SEQ ID NO 6
<211> LENGTH: 18
<212> TYPE: DNA
<213> ORGANISM: Homo sapiens

<400> SEQUENCE: 6
actaagtgtg ccagtggc                                                 18

<210> SEQ ID NO 7
<211> LENGTH: 20
<212> TYPE: DNA
<213> ORGANISM: Homo sapiens

<400> SEQUENCE: 7
gacggaaggc tgacaaggag                                               20

<210> SEQ ID NO 8
<211> LENGTH: 22
<212> TYPE: DNA
<213> ORGANISM: Homo sapiens

<400> SEQUENCE: 8
aggtcacagt cctgttgcaa ct                                            22

<210> SEQ ID NO 9
<211> LENGTH: 20
<212> TYPE: DNA
<213> ORGANISM: Homo sapiens

<400> SEQUENCE: 9
gaagtccctt gccatcctaa                                               20

<210> SEQ ID NO 10
<211> LENGTH: 20
<212> TYPE: DNA
<213> ORGANISM: Homo sapiens
```

-continued

```
<400> SEQUENCE: 10
gcacgaaggc tcatcattca                                        20
```

METHOD FOR DETECTING RP2-ARHGAP6 GENE

This application is a national stage filing under 35 U.S.C. § 371 of PCT/JP2016/074442, filed Aug. 23, 2016, which claims priority to U.S. Provisional Patent Application No. 62/209,130 filed Aug. 24, 2015, and Japanese Patent Application No. 248292/2015, filed Dec. 21, 2015, the contents of which are each incorporated herein by reference in their entireties.

This application incorporates-by-reference the sequence listing contained in the text file named OS10201_Sequence Listing.txt, which was created Feb. 8, 2018 and is 19.8 kb in size.

TECHNICAL FIELD

The present invention relates to a method for detecting a novel fusion gene.

BACKGROUND ART

The retinitis pigmentosa 2 (X-linked recessive) (RP2) gene exists on the short arm of the human chromosome X, and it is known as a causal gene of retinitis pigmentosa (Nat Genet. 1998; 19(4): 327-332). RP2 is known to have a function to bind to ARL3 (ADP ribosylation factor like GTPase 3), which is one of the small GTPase protein family members, to enhance GTP hydrolase activity of ARL3, i.e. it is a GTPase activating protein (Nat Struct Mol Biol. 2008; 15(4): 373-380). Its association with cancer is currently unknown.

Rho GTPase activating protein 6 (ARHGAP6) gene, which has GTPase activating function, exists on the short arm of human chromosome X, same as RP2, and the protein encoded by this gene is a GTPase activating protein possessing a Rho-GAP domain at the center. The ARHGAP6 gene is known to have a function of enhancing the GTP hydrolase activity of the small GTPase protein family, particularly RhoA (Hum Mol Genet. 2000; 9(4): 477-488). With regards to cancer, it is reported that the gene has decreased its expression in the African American population, which has a high incidence rate and mortaility rate of colon cancer (PLoS One. 2012; 7(1): e30168), and also that a fusion gene thereof with a claudin 18 (CLDN18) gene was found in patients suffered from diffuse type gastric cancer (Nature 2014; 513(7517): 202-209).

There are no reports so far of a fusion gene composed of RP2 and ARHGAP6.

SUMMARY OF INVENTION

Problem to be Solved by Invention

The object of the present invention is to elucidate a new causative gene of cancer, polynucleotide, and thereby provide a method for detecting a polynucleotide or a polypeptide that is encoded by the polynucleotide, as well as a primer set or a detection kit for such detection.

Means for Solving the Problems

The present inventors isolated and identified from stomach cancer cell line, a novel fusion gene in which a part of the ARHGAP6 gene and a part of the RP2 gene are fused together (Example 1), and found that this fusion gene was the causative gene of cancer, since the survival ratio of the stomach cancer cell line declined with the suppression of expression of fusion genes in stomach cancer cell lines that endogenously express such fusion genes (Example 2). The present inventors constructed a detection method of a fusion gene based on these findings, and provided primer sets for such purpose, thereby using the detection of such fusion gene made it possible to select cancer patients (particularly, stomach cancer patients) that test positive for a fusion gene composed of an RP2 gene and an ARHGAP6 gene (Example 3).

In other words, the present invention relates to [1] to [24] shown below.

[1] A method for detecting a fusion gene composed of a retinitis pigmentosa 2 (X-linked recessive) (RP2) gene and a Rho GTPase activating protein 6 (ARHGAP6) gene, the method comprising a step of detecting whether a polynucleotide that encodes a polypeptide described by either (1) or (2) shown below exists in a sample obtained from a subject:

(1) a polypeptide that comprises an amino acid sequence having no less than 90% identity with an amino acid sequence represented by SEQ ID NO: 2;

(2) a polypeptide that comprises an amino acid sequence represented by SEQ ID NO: 2, or a polypeptide that comprises an amino acid sequence represented by SEQ ID NO: 2, in which 1 to 10 amino acids are deleted, substituted, inserted and/or added.

[2] The method according to [1], wherein the polypeptide comprises an amino acid sequence having no less than 90% identity with an amino acid sequence represented by SEQ ID NO: 2, and has an ability to develop tumor

[3] The method according to [1], wherein the polypeptide comprises an amino acid sequence represented by SEQ ID NO: 2 and has an ability to develop tumor, or the polypeptide comprises an amino acid sequence represented by SEQ ID NO: 2, in which 1 to 10 amino acids are deleted, substituted, inserted and/or added, and has an ability to develop tumor.

[4] The method according to [1], wherein the polypeptide consists of an amino acid sequence represented by SEQ ID NO: 2.

[5] A method for detecting a fusion gene composed of an RP2 gene and an ARHGAP6 gene comprising a step of detecting whether a polynucleotide that encodes a polypeptide consisting of an amino acid sequence represented by SEQ ID NO: 2 exists in a sample obtained from a subject.

[6] The method according to any one of [1] to [5] further comprising a step in which it is judged when a polynucleotide targeted in detection is detected, that a fusion gene composed of an RP2 gene and an ARHGAP6 gene exists.

[7] The method according to any one of [1] to [6], further comprising a step of amplifying a nucleic acid existing in a sample obtained from a subject, or a step of hybridizing a probe with a nucleic acid existing in a sample obtained from a subject to detect a polynucleotide targeted in detection.

[8] The method according to [7] comprising a step of amplifying the nucleic acid existing in a sample obtained from a subject using a primer set shown below:

a primer set for detecting a fusion gene composed of an RP2 gene and an ARHGAP6 gene, the primer set comprising a sense primer designed from a section encoding RP2 and an antisense primer designed from a section encoding ARHGAP6, wherein the antisense primer consists of an oligonucleotide that hybridizes under a stringent condition with a polynucleotide targeted in detection, and the sense primer consists of an oligonucleotide that hybridizes under a stringent condition with a complementary strand of a polynucleotide targeted in detection.

[9] The method according to [8], wherein the sense primer consists of an oligonucleotide that hybridizes under a stringent condition with a complementary strand of a polynucleotide consisting of base no. 1 to 102 of SEQ ID NO: 1, and the antisense primer consists of an oligonucleotide that hybridizes under a stringent condition with a polynucleotide consisting of base no. 103 to 2439 of SEQ ID NO: 1.

[10] The method according to any one of [7] to [9] comprising a step of amplifying the nucleic acid existing in a sample obtained from a subject using a primer set shown below:

a primer set for detecting a fusion gene composed of an RP2 gene and an ARHGAP6 gene, wherein a sense primer consists of an oligonucleotide of at least 16 random consecutive bases between base no. 1 to 102 of SEQ ID NO: 1, and an antisense primer consists of an oligonucleotide complementary to an oligonucleotide of at least 16 random consecutive bases between base no. 103 to 2439 of SEQ ID NO: 1.

[11] The method according to any one of [7] to [10] further comprising a step of detecting whether an amplified nucleic acid fragment of a target size was obtained.

[12] The method according to [11] further comprising a step in which it is judged when an amplified nucleic acid fragment of a target size is obtained, that a fusion gene composed of an RP2 gene and an ARHGAP6 gene exists.

[13] The method according to any one of [7] to [10] further comprising a step of determining a base sequence of an amplified nucleic acid fragment.

[14] The method according to [13] further comprising a step in which it is judged when an amplified nucleic acid fragment includes a base sequence of a section encoding RP2 and a base sequence of a section encoding ARHGAP6 in a same fragment, that a fusion gene composed of an RP2 gene and an ARHGAP6 gene exists.

[15] The method according to [7] comprising a step of hybridizing a probe with the nucleic acid existing in a sample obtained from a subject, wherein the probe comprises an oligonucleotide that hybridizes with the polynucleotide under a stringent condition.

[16] The method according to [15] comprising a step of performing in situ hybridization using a sample obtained from a subject, a probe designed from a section encoding RP2 of the polynucleotide, and a probe designed from a section encoding ARHGAP6 of the polynucleotide.

[17] The method according to [16] using multiple types of probes designed from a section encoding RP2, and multiple types of probes designed from a section encoding ARHGAP6.

[18] The method according to [7], [16] or [17] using multiple types of adjacent probe pairs comprising an oligonucleotide that is complementary to an oligonucleotide of at least 16 random consecutive bases between base no. 1 to 102 of SEQ ID NO: 1, and multiple types of adjacent probe pairs comprising an oligonucleotide that is complementary to an oligonucleotide of at least 16 random consecutive bases between base no. 103 to 2439 of SEQ ID NO: 1, in a step of hybridizing a probe with the nucleic acid existing in a sample obtained from a subject.

[19] The method according to any one of [16] to [18] further comprising a step of amplifying hybridization signals.

[20] The method according to any one of [16] to [19] further comprising a step of detecting a signal overlap of a signal from a probe designed from a section encoding RP2 and a signal from a probe designed from a section encoding ARHGAP6.

[21] The method according to [20] further comprising a step in which it is judged when two signals are detected at a same area, that a fusion gene composed of an RP2 gene and an ARHGAP6 gene exists.

[22] The method according to any one of [1] to [21] comprising a step of obtaining a sample from a subject.

[23] The method according to any one of [1] to [22], wherein the subject is a cancer patient.

[24] The method according to [23], wherein cancer is stomach cancer.

Further, the present invention relates to [25] to [27] shown below.

[25] A method for detecting whether cancer exists in a subject comprising the step according to any one of [1] to [21].

[26] The method according to [25] comprising a step of obtaining a sample from a subject.

[27] The method according to [25] or [26], wherein cancer is stomach cancer.

Further, the present invention relates to [28] to [32] shown below.

[28] The method for diagnosing cancer in a subject comprising a step according to any one of [1] to [21].

[29] The method according to [28] comprising a step of obtaining a sample from a subject.

[30] The method according to [28] or [29] further comprising a step in which it is judged when a fusion gene composed of an RP2 gene and an ARHGAP6 gene is detected in a sample obtained from a subject, that there is a high possibility of the subject having cancer.

[31] The method according to [28] or [29], wherein cancer is stomach cancer.

[32] The method according to [29] further comprising a step in which it is judged when a fusion gene composed of an RP2 gene and an ARHGAP6 gene is detected in a sample obtained from a subject, that there is a high possibility of a subject having stomach cancer.

Further, the present invention relates to [33] to [36] shown below.

[33] A method for identifying a subject that is a candidate for receiving a treatment by an ARHGAP6 function inhibitor and/or a pharmaceutical agent for blcking an abnormal signal induced by a fusion gene composed of an RP2 gene and an ARHGAP6 gene, comprising a step according to any one of [1] to [21], wherein the subject is a cancer patient.

[34] The method according to [33] comprising a step of obtaining a sample from a subject.

[35] The method according to [33] or [34] further comprising a step in which it is judged when a fusion gene composed of an RP2 gene and an ARHGAP6 gene is detected in a sample obtained from a subject, that the subject is a candidate for receiving a treatment by an ARHGAP6 inhibitor and/or a pharmaceutical agent for blocking an abnormal signal induced by a fusion gene composed of an RP2 gene and an ARHGAP6 gene.

[36] The method according to any one of [33] or [35], wherein cancer is stomach cancer.

Further, the present invention relates to [37] to [42] shown below.

[37] A primer set for detecting a fusion gene composed of an RP2 gene and an ARHGAP6 gene existing in a sample obtained from a subject, the primer set comprising a sense primer designed from a section encoding RP2 and an antisense primer designed from a section encoding ARHGAP6, wherein the antisense primer consists of an oligonucleotide that hybridizes under a stringent condition with the polynucleotide according to any one of [1] to [5], and the sense primer consists of an oligonucleotide that hybridizes under a stringent condition with a complementary strand of the polynucleotide.

[38] The primer set according to [37], wherein the sense primer consists of an oligonucleotide that hybridizes under a stringent condition with a complementary strand of a polynucleotide consisting of base no. 1 to 102 of SEQ ID NO: 1, and the antisense primer consists of an oligonucleotide that hybridizes under a stringent condition with a polynucleotide consisting of base no. 103 to 2439 of SEQ ID NO: 1.

[39] A primer set for detecting a fusion gene composed of an RP2 gene and an ARHGAP6 gene existing in a sample obtained from a subject, the primer set comprising a sense primer designed from a section enconding RP2 or an antisense primer designed from a section encoding ARHGAP6 of the polynucleotide according to any one of [1] to [5].

[40] The primer set according to any one of [37] to [39], wherein the sense primer consists of an oligonucleotide of at least 16 random consecutive bases between base no. 1 to 102 of SEQ ID NO: 1, and the antisense primer consists of an oligonucleotide that is complementary to an oligonucleotide of at least 16 random consecutive bases between base no. 103 to 2439 of SEQ ID NO: 1.

[41] The primer set according to any one of [37] to [40], wherein the subject is a cancer patient.

[42] The primer set according to [41], wherein cancer is stomach cancer.

Further, the present invention relates to [43] to [48] shown below.

[43] A probe for detecting a fusion gene composed of an RP2 gene and an ARHGAP6 gene existing in a sample obtained from a subject, the probe comprising an oligonucleotide that hybridizes under a stringent condition with the polynucleotide according to any one of [1] to [5].

[44] The probe set comprising multiple probes according to [43], the probe set comprising a probe designed from a section encoding RP2 and a probe designed from a section encoding ARHGAP6 of the polynucleotide according to any one of [1] to [5].

[45] The probe set according to [44] comprising multiple types of probes designed from a section encoding RP2 and multiple types of probes designed from a section encoding ARHGAP6.

[46] The probe set according to [44] or [45] comprising multiple types of adjacent probe pairs comprising an oligonucleotide that is complementary to an oligonucleotide of at least 16 random consecutive bases between base no. 1 to 102 of SEQ ID NO: 1 and multiple types of adjacent probe pairs comprising an oligonucleotide that is complementary to an oligonucleotide of at least 16 random consecutive bases between base no. 103 to 2439 of SEQ ID NO: 1.

[47] The probe or a probe set according to any one of [43] to [46], wherein the subject is a cancer patient.

[48] The method according to [47], wherein cancer is stomach cancer.

Further, the present invention relates to [49] to [53] shown below.

[49] A detection kit for detecting a fusion gene composed of an RP2 gene and an ARHGAP6 gene existing in a sample obtained from the subject, the detection set comprising a primer set according to any one of [37] to [40].

[50] A detection kit for detecting a fusion gene composed of an RP2 gene and an ARHGAP6 gene existing in a sample obtained from a subject, the detection kit comprising a probe or a probe set according to any one of [43] to [46].

[51] The detection kit according to [50] further comprising a reagent for amplifying a signal of hybridization.

[52] The detection kit according to any one of [49] to [51], wherein the subject is a cancer patient.

[53] The detection kit according to [52], wherein cancer is stomach cancer.

Further, the present invention relates to [54] to [63] shown below.

[54] A detection method of a fusion protein of RP2 and ARHGAP6 comprising a step of detecting whether a polypeptide according to either (1) or (2) exists in a sample obtained from a subject:
(1) a polypeptide that comprises an amino acid sequence having no less than 90% identity with an amino acid sequence represented by SEQ ID NO: 2;
(2) a polypeptide that comprises an amino acid sequence represented by SEQ ID NO: 2, or a polypeptide that comprises an amino acid sequence represented by SEQ ID NO: 2, in which 1 to 10 amino acids are deleted, substituted, inserted and/or added.

[55] The method according to [54], wherein the polypeptide comprises an amino acid sequence having no less than 90% identity with an amino acid sequence represented by SEQ ID NO: 2, and has an ability to develop tumor.

[56] The method according to [54], wherein the polypeptide comprises an amino acid sequence represented by SEQ ID NO: 2 and has an ability to develop tumor, or the polypeptide comprises an amino acid sequence represented by SEQ ID NO: 2, in which 1 to 10 amino acids are deleted, substituted, inserted and/or added, and has an ability to develop tumor.

[57] The method according to [54], wherein the polypeptide consists of an amino acid sequence represented by SEQ ID NO: 2.

[58] A detection method of a fusion protein of RP2 and ARHGAP6 comprising a step of detecting whether a polypeptide consisting of an amino acid sequence represented by SEQ ID NO: 2 exists in a sample obtained from a subject.

[59] The method according to any one of [54] to [58], wherein the step for detecting whether the polypeptide exists comprises a step of bringing an antibody (primary antibody) that recognizes a section derived from an RP2 gene in the polypeptide and an antibody (primary antibody) that recognizes a section derived from an ARHGAP6 gene in the polypeptide in contact with a sample obtained from a subject.

[60] The method according to [59] further comprising steps of i) to v) described below:
i) a step of adding secondary antibodies that are connected to oligonucleotides and that respectively bind to primary antibodies; ii) a step of adding a ligation solution that contains two types of oligonucleotides that are partially complementary to oligonucleotides connected to the secondary antibodies and a ligase that can ligate the two types of oligonucleotides to form a circular structure when the oligonucleotides approach each other, thereby inducing a ligation reaction; iii) a step of elongating a nucleic acid along a circular structure that is formed; and iv) a step of hybridizing a labeled oligonucleotide probe that can hybridize with an elongated nucleic acid, and v) a step of detecting a labeled signal.

[61] The method according to any one of [54] to [60] comprising a step of obtaining a sample from a subject.

[62] The method according to any one of [54] to [61], wherein the subject is a cancer patient.

[63] The method according to [62], wherein cancer is stomach cancer.

Further, the present invention relates to [64] to [66] shown below.

[64] A method for detecting whether cancer exists in a subject comprising the step according to any one of [54] to [60].

[65] The method according to [64] comprising a step of obtaining a sample from a subject.

[66] The method according to [64] or [65], wherein cancer is stomach cancer.

Further, the present invention relates to [67] to [71] shown below.

[67] A method for diagnosing cancer in a subject comprising a step according to any one of [54] to [60].

[68] The method according to [67] comprising a step of obtaining a sample from a subject.

[69] The method according to [67] or [68] further comprising a step in which it is judged when a fusion protein of RP2 and ARHGAP6 is detected in a sample obtained from a subject, that there is a high possibility of the subject having cancer.

[70] The method according to [67] or [68], wherein cancer is stomach cancer. [71] The method according to [68] further comprising a step in which it is judged when a fusion protein of RP2 and ARHGAP6 is detected in a sample obtained from a subject, that there is a high possibility of the subject having stomach cancer.

Further, the present invention relates to [72] to [75] shown below.

[72] A method for identifying a subject that is a candidate for receiving a treatment by an ARHGAP6 function inhibitor and/or a pharmaceutical agent for blocking an abnormal signal induced by a fusion gene composed of an RP2 gene and an ARHGAP6 gene, the method comprising a step according to any one of [54] to [60], wherein the subject is a cancer patient.

[73] The method according to [72] comprising a step of obtaining a sample from a subject.

[74] The method according to [72] or [73] further comprising a step in which it is judged when a fusion protein of RP2 and ARHGAP6 is detected in a sample obtained from a subject, that the subject is a candidate for receiving a treatment by an ARHGAP6 inhibitor and/or a pharmaceutical agent for blocking an abnormal signal induced by a fusion gene composed of an RP2 gene and an ARHGAP6 gene.

[75] The method according to [72] or [74], wherein cancer is stomach cancer.

Further, the present invention relates to [76] to [79] shown below.

[76] A detection kit for detecting a fusion protein of RP2 and ARHGAP6 existing in a sample obtained from a subject, the detection kit comprising an antibody (primary antibody) that recognizes a section derived from an RP2 gene in the polypeptide according to any one of [54] to [58], and an antibody (primary antibody) that recognizes a section derived from an ARHGAP6 gene in said polypeptide.

[77] The detection kit according to [76] comprising secondary antibodies that are connected to oligonucleotides and that respectively bind to primary antibodies, two types of oligonucleotides that are partially complementary to the oligonucleotides connected to the secondary antibodies, a ligase that can ligate the two types of oligonucleotides to form a circular structure when the oligonucleotides approach each other, and a labeled oligonucleotide probe.

[78] The detection kit according to [76] or [77], wherein the subject is a cancer patient.

[79] The detection kit according to [78], wherein cancer is stomach cancer.

Further, the present invention relates to [80] to [81] shown below.

[80] A polypeptide according to any one of (1) to (3) shown below or a polynucleotide encoding said polypeptide:

(1) a polypeptide that comprises an amino acid sequence having no less than 90% identity with an amino acid sequence represented by SEQ ID NO: 2;

(2) a polypeptide that comprises an amino acid sequence represented by SEQ ID NO: 2, in which 1 to 10 amino acids are deleted, substituted, inserted and/or added;

(3) a polypeptide consisting of an amino acid sequence represented by SEQ ID NO: 2.

[81] The polypeptide or a polynucleotide encoding said polypeptide according to [80] that has an ability to develop tumor.

Advantageous Effect of Invention

The detection method of the present invention may be used as a method for detecting cancer (particularly, stomach cancer) that tests positive for a fusion gene composed of an RP2 gene and an ARHGAP6 gene (hereinafter referred to as RP2-ARHGAP6 fusion gene). The primer set, probe, probe set and detection kit of the present invention may be used in a detection method of the present invention.

BRIEF DESCRIPTION OF DRAWINGS

FIG. 2 compares the number of viable cells cultured in a 0.5% bovine serum containing RPMI-1640 medium after introduction of siRNA with that of the control.

DESCRIPTION OF EMBODIMENTS

«Detection Method of the Present Invention»

Figure 1:
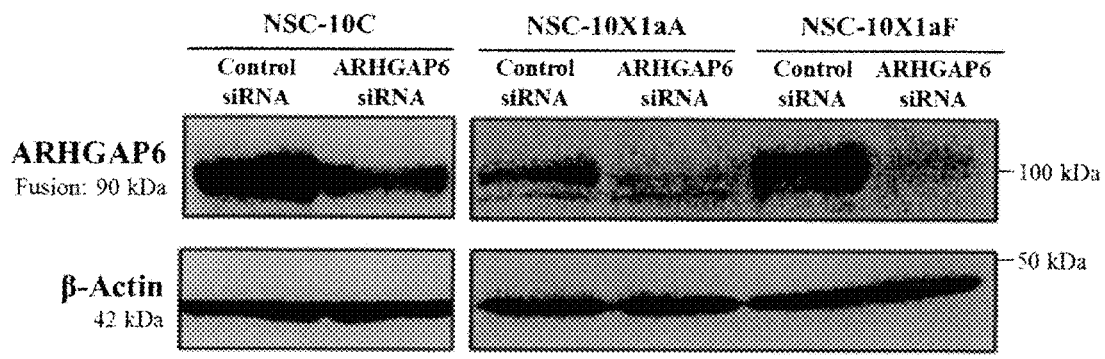
FIG. 1 shows the result of the Western blot. It shows the change in the amount of protein expression of the RP2-ARHGAP6 fusion protein by the ARHGAP6 siRNA treatment.

The detection method of the present invention includes a method for detecting a fusion gene, and a method for detecting a fusion protein encoded in the fusion gene. The method for detecting a fusion gene of the present invention or the method for detecting a fusion protein of the present invention includes a step of detecting whether a specific polynucleotide or polypeptide exists in a sample obtained from a subject.

Items collected from the subject (samples separated from a living body) are used as the sample obtained from the subject, specifically, any cells, tissues, or body fluids that were collected (blood, oral mucus, circulating tumor cells, exosome, etc.), biopsied samples (samples from the primary focus, cancer cells in the peritoneal lavage solution, cancer cells in ascites, etc.), of which the biopsied samples are preferred. It is possible to use genome DNAs extracted from the collected samples or to use transcription products thereof (products that are obtained by transcription and translation of a genome; e.g. RNA, protein) or cDNA prepared from RNA. It is particularly preferable to use RNA or cDNA that had been formulated. It is also possible to use a stabilized sample fixed in formalin and embedded in paraffin (Formalin-Fixed Paraffin-Embedded sample; FFPE Sample). A FFPE sample sliced into a thin FFPE slice may also be used. A use of a FFPE slice enables a direct detection of a polynucleotide existing in the slice.

The method for detecting a fusion gene in the present invention is a method for detecting "a fusion gene composed of an RP2 gene and an ARHGAP6 gene," wherein the fusion gene is a fusion gene comprising a part of an RP2 gene and a part of an ARHGAP6 gene. An exemplary fusion gene composed of an RP2 gene and an ARHGAP6 gene includes a polynucleotide consisting of a base sequence represented by SEQ ID NO: 1. The polynucleotide consisting of a base sequence represented by SEQ ID NO: 1 is a polynucleotide with a base sequence of base no. 190 (corresponding to the 5' terminal of the coding sequence (hereinafter referred to as CDS)) to 291 of an RP2 gene (GenBank registration no: NM 006915.2) and base no. 1462 to 3798 (corresponding to the 3' terminal of CDS) of an ARHGAP6 gene (GenBank registratioin no: NM 013427.2). Of the base sequence represented by SEQ ID NO: 1, the sequence from base no. 1 to 102 is derived from an RP2 gene, and the sequence from base no. 103 to 2439 is derived from an ARHGAP6 gene. The polynucleotide consisting of a base sequence represented by SEQ ID NO: 1 is also referred to as a "fusion polynucleotide." The amino acid sequence encoded in base no. 1 to 2439 of SEQ ID NO: 1 is shown in SEQ ID NO: 2.

In the "step of detecting whether a polynucleotide exists" in the detection method of a fusion gene of the present invention, the polynucleotide that is the target of detection (referred to in the present specification as the "polynucleotide targeted in detection") includes, for example, a polynucleotide encoding a polypeptide described in (1) or (2) shown below:

(1) a polypeptide that comprises an amino acid sequence having no less than 90% identity with an amino acid sequence represented by SEQ ID NO: 2;

(2) a polypeptide that comprises an amino acid sequence having no less than 90% identity with an amino acid sequence represented by SEQ ID NO: 2, and has an ability to develop tumor.

In the aforementioned polypeptide, the "identity with an amino acid sequence represented by SEQ ID NO: 2" is preferably 95% or higher, and more preferably 98% or higher.

Note that the "identity" as used in the present specification is a value of "Identity" obtained by using a parameter prepared by default by the NEEDLE program (J Mol Biol 1970; 48: 443-453) search. The aforementioned parameter is shown below.

Gap penalty=10
Extend penalty=0.5
Matrix=EBLOSUM62

Whether a polypeptide "has an ability to develop tumor" or not may be confirmed by a method shown below in Example 2. One specific method is to introduce siRNA that suppresses the expression of a polynucleotide encoding the polypeptide to a cell expressing the polypeptide (NSC-10C), and to verify that the viability of the cell decreases.

In one embodiment of the present invention, the polynucleotide targeted in detection is a polynucleotide encoding a polypeptide according to any one of (1) to (4) shown below:

(1) a polypeptide that comprises an amino acid sequence represented by SEQ ID NO: 2, in which 1 to 10 amino acids are deleted, substituted, inserted and/or added;

(2) a polypeptide that comprises an amino acid sequence represented by SEQ ID NO: 2, in which 1 to 10 amino acids are deleted, substituted, inserted and/or added, and has an ability to develop tumor;

(3) a polypeptide that comprises an amino acid sequence represented by SEQ ID NO: 2 and has an ability to develop tumor; and (4) a polypeptide that consists of an amino acid sequence represented by SEQ ID NO: 2.

In the polypeptide of (1) and (2), the number of amino acids that had been deleted, substituted, inserted and/or added in the amino acid sequence represented by SEQ ID NO: 2 is preferably one to a few, more preferably 1 to 7, and even more preferably 1 to 5.

An example of a polynucleotide that encodes "a polypeptide that consists of an amino acid sequence represented by SEQ ID NO: 2" includes "a polynucleotide that consists of a base sequence represented by SEQ ID NO: 1."

The method for detecting a fusion gene of the present invention may comprise a step in which it is judged whether the polynucleotide targeted in detection exists by whether said polynucleotide was detected.

The method for detecting a fusion gene of the present invention may further comprise a step in which it is judged when a polynucleotide targeted in detection is detected, that a fusion gene composed of an RP2 gene and an ARHGAP6 gene exists.

The method for detecting a fusion gene of the present invention may comprise a step of amplifying the nucleic acid existing in the sample obtained from a subject or a step of hybridizing a probe with the nucleic acid existing in the sample obtained from a subject to detect the polynucleotide targeted in detection.

The nucleic acid to be used may be a genome DNA, RNA or a cDNA prepared from RNA. The methods of extracting DNA, extracting RNA or preparing cDNA from RNA is commonly known in the field, and it may be performed easily by using a commercially available DNA extraction kit, RNA extraction kit or a cDNA synthesis kit.

The step of amplifying a nucleic acid in the sample obtained from a subject may be performed by a commonly known method of amplifying a nucleic acid. Such method includes PCR (Polymerase chain reaction, e.g. realtime PCR), LCR (Ligase chain reaction), SDA (Strand displacement amplification), NASBA (Nucleic acid sequence-based amplification), ICAN (Isothermal and chimeric primer-initiated amplification of nucleic acids), LAMP (Loop-mediated isothermal amplification), TMA (Transcription-mediated amplification, e.g. Gen-Probe's TMA system), and a preferable method is PCR.

Specifically, the nucleic acid (e.g. genome DNA, RNA, or cDNA prepared from RNA, etc.) in the sample obtained from a subject is subjected to a nucleic acid amplification reaction using a primer set designed to specifically amplify a polynucleotide targeted in detection. The primer set to be used is not particularly limited as long as it can specifically amplify the polynucleotide targeted in detection. For example, a use of a primer design software (e.g. Primer Express; Applied Biosystems) allows a person skilled in the art to easily design the primer set based on the base sequence of the polynucleotide targeted in detection. More specifically, a primer set includes a sense primer (5'-primer) designed from a section that encodes the RP2 of a polynucleotide targeted in detection (e.g. any section in an RP2 gene region of the fusion polynucleotide (particularly, cDNA)) and an antisense primer (3'-primer) designed from a section encoding ARHGAP6 of a polynucleotide targeted in detection (e.g. any section in an ARHGAP6 gene region of the fusion polynucleotide (particularly, cDNA)), and the antisense primer consists of an oligonucleotide that hybridizes with a polynucleotide targeted in detection under a stringent condition (preferably, under a highly stringent condition), and the sense primer consists of an oligonucleotide that hybridizes with a complementary strand of a polynucleotide targeted in detection under a stringent condition (preferably, under a highly stringent condition). Otherwise, either the sense primer or the antisense primer may be designed so that it corresponds to the region comprising the fusion point of the polynucleotide targeted in detection.

The "stringent condition" in the present specification refers to a hybridization condition of "5×SSPE, 5×Denhardt's solution, 0.5% SDS, 50% formaldehyde, 200 µg/mL salmon sperm DNA, at 42° C. overnight" and a washing condition of "0.5×SSC, 0.1% SDS, 42° C." "A highly stringent condition" refers to a hybridization condition of "5×SSPE, 5×Denhardt's solution, 0.5% SDS, 50% formaldehyde, 200 µg/mL salmon sperm DNA, at 42° C. overnight" and a washing condition of "0.2×SSC, 0.1% SDS, 65° C."

The "fusion point" of a polynucleotide targeted in detection in the present specification is a point in which a section derived from an RP2 gene and a section derived from an ARHGAP6 gene in the polynucleotide targeted in detection are fused together, and the "region comprising the fusion point" in the polynucleotide targeted in detection is, for example, the region comprising bases of base no. 102 and 103 when the polynucleotide targeted in detection is a polynucleotide consisting of a base sequence represented by SEQ ID NO: 1.

In an embodiment of the present invention, the sense primer consists of an oligonucleotide hybridizing with a complementary strand of a polynucleotide that consists of base no. 1 to 102 of SEQ ID NO: 1 under a stringent condition, and the antisense primer consists of an oligonucleotide hybridizing with a polynucleotide that consists of base no. 103 to 2439 of SEQ ID NO: 1 under a stringent condition.

In an embodiment of the present invention, the sense primer consists of at least 16 consecutive bases of an oligonucleotide between base no. 1 to 102 of SEQ ID NO: 1, and the antisense primer consists of an oligonucleotide that is complementary with at least 16 consecutive bases of an oligonucleotide that consists of base no. 103 to 2439 of SEQ ID NO:

In a step to amplify nucleic acid, the sense primer and the antisense primer should preferably be set so that the fragment size of the nucleic acid to be amplified is 1 kb or lower, since a large fragment size of the nucleic acid to be amplified leads to poor amplification efficiency. The primers to be used generally have a chain length of at least 15 bases, preferably at least 16 bases, more preferably at least 18 bases, even more preferably at least 20 bases. In one embodiment of the present invention, the primer has 15 to 40 bases, preferably 16 to 24 bases, more preferably 18 to 24 bases, even more preferably 20 to 24 bases.

The primer may be produced by chemical synthesis without being particularly limited thereby.

In a preferable embodiment, the detection method of a fusion gene of the present invention further encompasses a step of detecting whether an amplified nucleic acid fragment of a desired size was obtained in addition to a step of amplifying nucleic acid in the sample obtained from a subject. The step of detecting whether an amplified nucleic acid fragment of a desired size was obtained may be performed using electrophoresis, for example. By using electrophoresis, the nucleic acid fragment may be analyzed by agarose gel electrophoresis to confirm whether amplified nucleic acid fragments were produced in the desired size by using ethidium bromide dye, etc.

Further, by performing a PCR amplification monitor in the amplification process of the gene (real time PCR) (Genome Res. 1996; 6(10): 986-994), it is possible to perform a quantified analysis of amplified nucleic acid fragments. A possible candidate to be used in the PCR amplification monitoring method is ABI PRISM7900 (Applied Biosystems).

When an amplified nucleic acid fragment of the desired size is obtained, that means that a polynucleotide targeted in detection existed in the sample obtained from a subject. The detection method of a fusion gene of the present invention may further include a step in which it is judged when an amplified nucleic acid fragment of the desired size is obtained, that a fusion gene composed of an RP2 gene and an ARHGAP6 gene exists.

In a separate preferable embodiment, the detection method of the fusion gene of the present invention further encompasses a step of determining the base sequence of the amplified nucleic acid in addition to a step of amplifying the nucleic acid of the sample obtained from a subject. The step of determining the base sequence of the nucleic acid fragment may use sequencing methods commonly known in the field of art including next generation sequencing methods (Nature Biotechnology 2008; 26: 1135-1145) (e.g. HiSeq2500 (Illumina)), such as the Sanger sequencing (e.g. ABI PRISM3100 (Applied Biosystems) may be used), or sequencing by synthesis, etc.

The step of determining the base sequence of the nucleic acid fragment includes not just a step of sequencing the full length of a nucleic acid fragment, but a step of sequencing partial sequences corresponding to both ends of the nucleic acid fragment.

When the sequenced nucleic acid fragment includes a base sequence of a section encoding RP2 and a base sequence of a section encoding ARHGAP6 of the polynucleotide targeted in detection in the same fragment, that means that the polynucleotide targeted in detection existed in the sample obtained from a subject. The detection method of the fusion gene of the present invention may further include a step in which it is judged when the amplified nucleic acid fragment includes a base sequence of a section encoding RP2 and a base sequence of a section encoding ARHGAP6 of the polynucleotide targeted in detection in the same fragment, that a fusion gene composed of an RP2 gene and an ARHGAP6 gene exists.

The step of hybridizing a probe with a nucleic acid in the sample obtained from a subject may be performed using a probe including an oligonucleotide that hybridizes under a stringent condition (preferably, under a highly stringent condition) with a polynucleotide targeted in detection, and using a commonly known hybridization method. Such methods include, for example, Northern hybridization, dot blot method, DNA micro array method, RNA protection method, in situ hybridization, etc. A preferable method is the in situ hybridization. Detection using the in situ hybridization may be performed by a commonly known fluorescent in situ hybridization (FISH), chromogenic in situ hybridization (CISH), or silver in situ hybridization (SISH). The chain length of the probe used in hybridization may be selected as necessary by a person skilled in the art according to the hybridization method to be used, but the probe preferably has a chain length of at least 16 bases.

In one embodiment of the present invention, the probe used in hybridization is an oligonucleotide that hybridizes under a stringent condition (preferably, under a highly stringent condition) with a polynucleotide targeted in detection, or a complementary strand thereof, and it includes an oligonucleotide of at least 16 bases upstream and at least 16 bases downstream of the fusion point on the polynucleotide targeted in detection (a specific example being a sequence of base no. 87 to 118 in SEQ ID NO: 1) or an oligonucleotide that is complementary to said oligonucleotide.

In one embodiment of the present invention, the step of hybridizing a probe with a nucleic acid existing in a sample obtained from a subject may be performed according to the commonly known RNA FISH method (J. Mol. Diagn. 2012; 14(1): 22-29). More specifically, in situ hybridization is performed using a sample obtained from a subject (e.g. FFPE fragment), a probe designed from a section encoding RP2 of the polynucleotide targeted in detection (e.g. any section in an RP2 gene region of the fusion polynucleotide), and a probe designed from a section encoding ARHGAP6 of the polynucleotide targeted in detection (e.g. any section in an ARHGAP6 gene region of the fusion polynucleotide). The probes include oligonucleotides that hybridize under a stringent condition (preferably, under a highly stringent condition) with the polynucleotide targeted in detection.

In one embodiment of the present invention, the in situ hybridization is performed using multiple detection probes designed from a section encoding RP2 and multiple detection probes designed from a section encoding ARHGAP6.

In one embodiment of the present invention, the in situ hybridization is performed using the following probes:

multiple types of adjacent probe pairs including oligonucleotides that are complementary to at least 16 random consecutive oligonucleotides in base no. 1 to 102 of SEQ ID NO: 1 (preferably 10 to 25 types, more preferably 18 to 22 types, even more preferably 20 types of probe pairs), and multiple types of adjacent probe pairs including oligonucleotides that are complementary to at least 16 random consecutive oligonucleotides in base no. 103 to 2439 of SEQ ID NO: 1 (preferably 10 to 25 types, more preferably 18 to 22 types, even more preferably 20 types of probe pairs).

In a further embodiment, the probe pair to be used in the in situ hybridization may include an adjacent probe pair including an oligonucleotide that is complementary to an oligonucleotide of at least 16 random consecutive bases in the nontranslating region on the 5' side of the RP2 gene (base no. 1 to 189 of GenBank registratioin no: NM 006915.2), and/or a probe pair including an oligonucleotide that is complementary to an oligonucleotide of at least 16 random consecutive bases in the nontranslating region on the 3' side of the ARHGAP6 gene (base no. 3799 to 5118 of GenBank registratioin no: NM 013427.2).

The "adjacent probe pairs" in the present specification consist of two types of probes that are arranged next to each other when they hybridize with the polynucleotide targeted in detection. The probes include an oligonucleotide that is complementary to the polynucleotide targeted in detection, and the length of the oligonucleotide is generally at least 16 bases, preferably at least 18 bases. In one embodiment of the present invention, the length of the oligonucleotide is 16 to 30 bases, preferably 18 to 25 bases.

In a preferable embodiment of the present invention, the detection method of the fusion gene of the present invention further encompasses a step of amplifying a hybridization signal in addition to a step of performing in situ hybridization. To perform a step of amplifying a hybridization signal, a reagent that amplifies a hybridization signal may be hybridized with a probe that hybridizes with a nucleic acid contained in the sample.

Reagents that amplify a hybridization signal used in in situ hybridization include PreAmplifier Mix QT, Amplifier Mix QT, Label Probe Mix, and Label Probe Diluent QF, which may be obtained from Affymetrix.

In a more preferable embodiment, the detection method of the fusion gene of the present invention further encompasses a step of detecting a signal overlap between a signal from a probe designed from a section encoding RP2 and a signal from a probe designed from a section encoding ARHGAP6. By separating the fluorescent reagent or the color reagent that detects a probe designed from a section encoding RP2 and a probe designed from a section encoding ARHGAP6, it is possible to observe whether the signals from the two different probes are in the same area (inside the same molecule). When it is observed that the signals from the two different probes are in the same area (inside the same molecule), that would mean that the polynucleotide targeted in detection existed in the sample obtained from a subject. The detection method of the fusion gene of the present invention may further include a step in which it is judged when the two signals are in the same area (inside the same molecule), that a fusion gene composed of an RP2 gene and an ARHGAP6 gene exists.

The probes are not particularly limited, but they may be produced by a chemical synthesis method.

The detection method of the fusion protein of the present invention is a method for detecting "a fusion protein of RP2 and ARHGAP6" and the fusion protein is a fusion protein encoded by the fusion gene of the RP2 gene and the ARHGAP6 gene.

In the "step of detecting whether polypeptide exists" in the detection method of the fusion protein of the present invention, the polypeptide targeted in detection includes a polypeptide that is encoded by a polynucleotide targeted in detection.

The detection method of the fusion protein of the present invention may encompass a step in which it is judged whether a polynucleotide exists by whether the polypeptide targeted in detection is detected.

The detection method of the fusion protein of the present invention may further encompass a step in which it is judged when the polypeptide targeted in detection is detected, that a fusion protein of RP2 and ARHGAP6 exists.

The step of detecting whether a polypeptide exists may be performed by preparing a lysate derived from a sample obtained from a subject (e.g. cancer tissue or cell obtained from a subject) and measuring the polypeptide targeted in detection, contained in the sample by an immunological measurement method or an enzyme active measurement method, which combine antibodies against proteins that constitute the fusion protein, or a detection method that combines these methods, or by mass spectrometry. Further, this step may be performed by a detection method using an immunological tissue staining technology performed by combining the polypeptide targeted in detection, included in the sample (e.g. FFPE fragment) obtained from a subject, that had undergone appropriate pretreatment (such as, removal of paraffin), with the antibodies against proteins constituting the fusion protein. Otherwise, this step may be performed by exchanging the antibodies against proteins constituting the fusion protein to antibodies that recognize the fusion section of the fusion protein. Exemplary approaches to these methods include the following methods using monoclonal antibodies and polyclonal antibodies specific to the polypeptide targeted in detection: enzyme immunizing measurement, double antibody sandwich ELISA method, fluorescent immunological measurement method, radioimmunological measurement method, Western blot, immunohistologic staining, a detection method combining immune precipitation and mass spectrometry, etc.

The "fusion section" of the fusion protein of the present specification refers to a section in the polypeptide targeted in detection, in which the section derived from an RP2 gene and a section derived from an ARHGAP6 gene are fused.

The detection using an immunohistologic staining technology may be performed according to Proximity Ligation Assay (Nat. Methods. 2006; 3(12): 995-1000). More specifically, whether the polypeptide targeted in detection exists or not may be detected by using an antibody that recognizes a section derived from the RP2 gene of the polypeptide targeted in detection, and an antibody that recognizes a section derived from an ARHGAP6 gene of a polypeptide targeted in detection, and by detecting that the two antibodies recognize the same molecule by the aforementioned technologies. More specifically, the detection may be performed by i) a step of bringing an antibody (primary antibody) that recognizes a section derived from an RP2 gene of the polypeptide targeted in detection, and the antibody (primary antibody) that recognizes a section derived from an ARHGAP6 gene of the polypeptide targeted in detection, in contact with the sample obtained from the subject; ii) a step of adding secondary antibodies that are connected to oligonucleotides, and binds to the respective primary antibodies, iii) a step of inducing ligation by adding two types of oligonucleotides that are partly complementary to the oligonucleotides connected to the secondary antibodies, and a ligation solution containing ligase that can form a circular structure by ligation of the two types of oligonucleotides when they approach each other; iv) a step of elongating a nucleic acid along the circular structure that was formed, v) a step of hybridizing a labeled oligonucleotide probe that can hybridize with the elongated nucleic acid; and vi) a step of detecting the labeling signal. Such detection may be performed using a PLA probe and reagents included in the Duolink II reagent kit or the Duolink II Bright field reagent kit (Olink).

In one embodiment of the present invention, the detection method of the present invention encompasses a step of obtaining a sample from the subject.

In one embodiment of the present invention, the subject of the detection method of the present invention is a cancer patient, and in a more specific embodiment, the cancer is stomach cancer. The type of stomach cancer is not particularly limited, but it may be a diffuse type, an intestinal type, or a mix type in the Lauren classification. Further, without being limited thereby, the stomach cancer may be any of papillary adenocarcinoma, tubular adenocarcinoma, poorly differentiated adenocarcinoma, signet ring cell carcinoma, or carcinoma mucoides, etc.

In the detection method of the present invention, it is possible to judge when the polynucleotide targeted in detection, or the polypeptide targeted in detection is detected in the sample obtained from the subject, that the subject has cancer (particularly, stomach cancer).

The detection step in the detection method of the present invention may be used as a method for detecting whether cancer (particularly, stomach cancer) exists in a subject or a method for diagnosing cancer (particularly, stomach cancer) in the subject. The diagnosis method of the present invention may include, in addition to the aforementioned detection step, a step in which it is judged when the polynucleotide targeted in detection, or the polypeptide targeted in detection is detected in the sample obtained from the subject, that there is a high possibility that the subject has cancer (particularly, stomach cancer). Further, the detection step may be used in a method for identifying a subject (cancer patients of stomach cancer, etc.) that is a candidate for receiving a treatment by an ARHGAP6 function inhibitor and/or a pharmaceutical agent that blocks abnormality signal induced by a fusion gene composed of an RP2 gene and an ARHGAP6 gene. The identification method of the present invention may include, in addition to the detection step, a step in which it is judged when a polynucleotide is detected in a sample obtained from the subject, that the subject is a candidate for receiving a treatment by an ARHGAP6 function inhibitor and/or a pharmaceutical agent that blocks abnormality signal induced by a fusion gene composed of an RP2 gene and an ARHGAP6 gene.

«The Primer Set, Probe, Probe Set and Detection Kit of the Present Invention»

The present invention encompasses a primer set, probe, probe set and a detection kit used in the detection method of the present invention.

The primer set of the present invention includes a sense primer designed from a section encoding RP2 and an antisense primer designed from a section encoding ARHGAP6, and the antisense primer consists of an oligonucleotide that hybridizes with the polynucleotide targeted in detection under a stringent condition (preferably, under a highly stringent condition), and the sense primer consists of an oligonucleotide that hybridizes with a complementary strand of a polynucleotide targeted in detection under a stringent condition (preferably, under a highly stringent condition).

In the primer set of the present invention, either the sense primer or the anti sense primer may be designed so that it corresponds to a region in a polynucleotide targeted in detection that comprises a fusion point.

A specific embodiment of the primer set of the present invention includes the following primer set:

a primer set consisting of a sense primer consisting of an oligonucleotide that hybridizes under a stringent condition with a complementary strand of a polynucleotide consisting of base no. 1 to 102 of SEQ ID NO: 1 and an antisense primer consisting of an oligonucleotide that hybridizes under a stringent condition with a polynucleotide consisting of base no. 103 to 2439 of SEQ ID NO: 1.

A more specific embodiment of the primer set of the present invention includes the following primer set:

a primer set consisting of a sense primer consisting of an oligonucleotide of at least 16 random consecutive bases between base no. 1 to 102 of SEQ ID NO: 1 and an antisense primer consisting of an oligonucleotide that is complementary with at least 16 random consecutive bases between base no. 103 to 2439 of SEQ ID NO: 1.

It is preferable for the primer set to have a space of 1 kb or lower between the selected positions of the sense primer and the anti sense primer, or a nucleic acid fragment amplified by the sense primer and the antisense primer with a size of 1 kb or lower. Further, the primer of the present invention normally has a chain length of at least 15 bases, preferably at least 16 bases, more preferably at least 18 bases, even more preferably at least 20 bases. In one embodiment of the present invention, the primer has a chain length of 15 to 40 bases, preferably 16 to 24 bases, more preferably 18 to 24 bases, and even more preferably 20 to 24 bases.

The primers included in the primer set of the present invention, without being particularly limited, may be produced by a chemical synthesis method.

The probes included in the probe of the present invention and the probe set of the present invention includes an oligonucleotide that hybridizes with the polynucleotide targeted in detection under a stringent condition (preferably, under a highly stringent condition). The chain length of the probes included in the probe of the present invention or the probe set of the present invention may be selected as necessary by a person skilled in the art according to the applied hybridization method, but the probe preferably has a chain length of at least 16 bases.

In one embodiment of the present invention, the probe of the present invention includes an oligonucleotide of at least 16 bases upstream and at least 16 bases downstream of the fusion point in the polynucleotide targeted in detection (specifically, the sequence between base no. 87 to 118 of SEQ ID NO: 1), or an oligonucleotide that is complementary thereto.

In one embodiment of the present invention, the probe set of the present invention includes a probe designed from a section encoding RP2 (e.g. any section in the RP2 gene region of the fusion polynucleotide) and a probe designed from a section encoding ARHGAP6 (e.g. any section in the ARHGAP6 gene region of the fusion polynucleotide).

In one embodiment of the present invention, the probe set of the present invention includes multiple types of probes designed from a section encoding RP2 and multiple types of probes designed from a section encoding ARHGAP6.

In one embodiment of the present invention, the probe set of the present invention includes the following:

multiple types of adjacent probe pairs including an oligonucleotide that is complementary to an oligonucleotide of at least 16 random consecutive bases between base no. 1 to 102 of SEQ ID NO: 1 (preferably 10 to 25 types, more preferably 18 to 22 types, even more preferably 20 types of probe pairs), and multiple types of adjacent probe pairs including an oligonucleotide that is complementary with an oligonucleotide of at least 16 random consecutive bases between base no. 103 to 2439 of SEQ ID NO: 1 (preferably 10 to 25 types, more preferably 18 to 22 types, even more preferably 20 types of probe pairs).

The probes of the probe pair include an oligonucleotide that is complementary with the polynucleotide targeted in detection, and the length of the oligonucleotide is normally at least 16 bases, preferably at least 18 bases. In one embodiment of the present invention, the length of the oligonucleotide is 16 to 30 bases, preferably 18 to 25 bases.

The probe of the present invention and the probe included in the probe set of the present invention, without being limited thereby, may be produced by chemical synthesis.

The present invention encompasses a detection kit including a primer set of the present invention, a probe of the present invention or the probe set of the present invention. The detection kit of the present invention may include in addition to the primer set of the present invention, the probe of the present invention or the probe set of the present invention, components that may be used together with the primer set, the probe or the probe set for the detection of a polynucleotide targeted in detection such as reagents to amplify the signal of hybridization.

The present invention also encompasses a detection kit for detecting a polypeptide targeted in detection. Preferably, the detection kit includes an antibody (primary antibody) that recognizes a section derived from an RP2 gene of polypeptide targeted in detection, and an antibody (primary antibody) that recognizes a section derived from an ARHGAP6 gene of polypeptide targeted in detection. More preferably, the present invention may include secondary antibodies connected with oligonucleotides, that are respectively bound to primary antibodies, two types of oligonucleotides that are partially complementary to the oligonucleotides connected to the secondary antibodies, ligase that forms a circular structure by ligation of the two types of oligonucleotides when they approach each other, and labeled oligonucleotide probes.

The primer set, probe, probe set, and detection kit of the present invention may be used for the detection method, diagnosis method, identification method of a patient, and identification method of a subject of the present invention. In one embodiment of the present invention, with respect to the primer set, probe, probe set and detection kit of the present invention, the subject is a cancer patient and more specifically, the cancer is stomach cancer. The stomach cancer is not particularly limited, but it may be a diffuse type, an intestinal type, or a mix type in the Lauren classification. Further, without being limited thereby, the stomach cancer may be any of papillary adenocarcinoma, tubular adenocarcinoma, poorly differentiated adenocarcinoma, signet ring cell carcinoma, or carcinoma mucoid.

EXAMPLES

The Examples may be performed by commonly known methods unless otherwise indicated. When using commercially available reagents or kits, the Examples may be performed according to the manuals of the commercial products.

Example 1 Isolation of RP2-ARHGAP6 Fusion Gene

Total RNA was prepared from stomach cancer cell line NSC-10C established at the Division of Translational Oncology, National Cancer Center Research Institute, and reverse-transcribed into cDNA with reverse transcriptase (SuperScriptIII; Life Technologies) and Oligo(dT) Primer (Oligo(dT)20 Primer; Life Technologies) according to the standard protocol of the reagent.

Next, primers of RP2_full fwd01 represented by SEQ ID NO: 3 and ARHGAP6_full rev01 represented by SEQ ID NO: 4 were used to perform PCR (10 sec. at 98° C., 15 sec. at 55° C., and 3 min. at 68° C., 30 cycles, followed by 5 min. at 68° C.) using DNA polymerase (PrimeSTAR GXL; TAKARA BIO INC.) with cDNA obtained in the above step as a template. Then, using the aforementioned PCR product diluted by 10-fold as a template, primers of RP2_full fwd02 represented by SEQ ID NO: 5 and ARHGAP6_full rev02 represented by SEQ ID NO: 6 were subjected to PCR (10 sec. at 98° C., 15 sec. at 55° C., and 3 min. at 68° C., 30 cycles, followed by 5 min. at 68° C.) using the same DNA polymerase. Electrophoresis was performed after the PCR to obtain PCR product of about 2.5 kbp. After adding A to the 3'-end of the PCR product using Takara Taq (TAKARA BIO INC.), it was cloned into a cloning vector (TOPO XL PCR Cloning Kit; Life Technologies), and sequenced by dideoxy sequencing method (BigDye Terminator v3.1 Cycle Sequencing Kit; Life Technologies). Consequently, the PCR product about 2.5 kbp derived from the NSC-10C cell line was found to be a transcription product (SEQ ID NO: 1) in which nucleotide sequence of base no. 190 (corresponding to the 5' terminal of CDS) to 291 of RP2 (NM 006915.2) registered in NCBI is fused to a nucleotide sequence of base no. 1462 to 3798 of ARHGAP6 (NM 013427.2) (corresponding to the 3' terminal of CDS). The amino acid sequence of a polypeptide encoded in SEQ ID NO: 1 is represented by SEQ ID NO: 2.

Example 2 Evaluation of Ability to Suppress Expression of RP2-ARHGAP6 Fusion Protein in Stomach Cancer Cell Lines Expressing RP2-ARHGAP6 Fusion Gene Using ARHGAP6 siRNA, and Evaluation of Viability of Those Cell Lines Under the Same Condition After culturing the cell line NSC-10C that expresses RP2-ARHGAP6 fusion gene, as shown in Example 1, and two substrains, NSC-10X1aA and NSC-10X1aF, established at the Division of Translational Oncology, National Cancer Center Resesarch Institute, in RPMI-1640 medium (Wako Pure Chemical Industries, Ltd.) containing 10% bovine serum (Gibco), siRNA was introduced into the cells according to the standard protocol of the transfection reagent DharmaFECT1 (GE Healthcare). Specifically, the above cancer cells were seeded at $2\times10^5$ cells per well to a 6 well plate (140675, Nunc), 75 pmol of siRNA that targets ARHGAP6 (288604, Life Technologies) and control siRNA (AM4611, Life Technologies) were added to the cells (final concentration 75 nM), and the cells were cultured at 37° C. under an environment of 5% $CO_2$ for 120 h. (hereinafter, the group in which control siRNA was transfected is referred to as the Control siRNA group, and the group in which siRNA that targets ARHGAP6 is transfected is referred to as the ARHGAP6 siRNA group).

The suppressive effect of RP2-ARHGAP6 fusion protein by siRNA treatment was evaluated by the Western blot analysis. Specifically, the cultured cells were dissolved in 350 mM dithiothreitol (Fermentas)-containing Laemmli Sample Buffer (Bio-Rad) to extract protein. Protein concentration was measured by Protein Quantification Assay (MACHEREY-NAGEL GmbH & Co. KG). 5 ug or 20 ug of the protein extract was loaded onto a 8% or 12% Poly-Acrylamide gel (Serva) containing SDS (Wako Pure Chemical Industries, Ltd.) and gel electrophoresis was performed for 1 h. under a condition of 40 mA. After 80 min. of trasnfer to a PVDF membrane (Millipore Corporation) under a 60 mA condition using TRANS-BLOT SD SEMI-DRY TRANSFER CELL (Bio-Rad), blocking was performed for 2 h. at room temperature using PBS containing 5% Membrane Blocking Agent (GE Healthcare) (hereinafter referred to as the blocking buffer). The membrane was shaken in a primary antibody solution of anti-ARHGAP6 antibody (HPA036779, Sigma-Aldrich) diluted with a blocking buffer to a rate of 1:250 and anti-β-Actin antibody (4967, Cell Signaling Technology) diluted with a blocking buffer to a rate of 1:3000, and incubated overnight at 4° C. After washing with PBS containing 0.05% Tween 20 (Wako Pure Chemical Industries, Ltd.) (hereinafter referred to as the washing buffer), the membrane was shaken in a secondary antibody solution of HRP labeled anti-rabbit antibody (P0399, Daco) diluted with a blocking buffer to a rate of 1:3000, and incubated for 1 h. at room temperature. After washing with a washing buffer, Pierce Western blot Substrate Plus (Thermo Fisher Scientific Inc.) was added onto the membrane, and the chemiluminescence on a membrane was detected using LAS-4000R (Fuji Film). Western blotting analysis confirmed that the expression of RP2-ARHGAP6 fusion protein was suppressed by the siRNA for ARHGAP6 in all cell lines that endogeneously expressed RP2-ARHGAP6 fusion gene (FIG. 1).

In order to evaluate the effect of the RP2-ARHGAP6 fusion gene on the viability of the cancer cells, siRNA that targets ARHGAP6 and the control siRNA were transfected into the the NSC-10C and the substrain thereof under the same conditions as shown above. After 24 h., the medium was changed to RPMI-1640 medium containing 0.5% bovine serum, and the cells were seeded at $1\times10^3$ cells per well to a 96 well plate (167008, Nunc), at 100 μL each, so that cells of each group were seeded to 6 wells, and cultured for additional 96 h. at 37° C. under a 5% $CO_2$ environment. Wells containing only RPMI-1640 medium containing 10% bovine serum without cells was prepared as a control (hereinafter referred to as the medium group). The number of living cells was measured according to the standard protocol of Cell Counting Kit-8 (DOJINDO LABORATORIES). Specifically, 10 μL of the reagent was added per well and the cells were cultured for 4 h. at 37° C. under a 5% $CO_2$ environment, then, the number of living cells was determined by measuring an absorbance of 450 nm by a micro plate reader (BioTek). Total 4 wells excluding the maximum and the minimum absorbance values of each group were adopted for the analysis. Viability of the Control siRNA group and the ARHGAP6 siRNA group was determined by subtracting the absorbance of the medium group from the absorbance of each group (hereinafter referred to as the correction value), and setting the correction value of the Control siRNA group as 100%. Student's t-test was used for the significance test between Control siRNA group and ARHGAP6 siRNA group.

Figure 2:
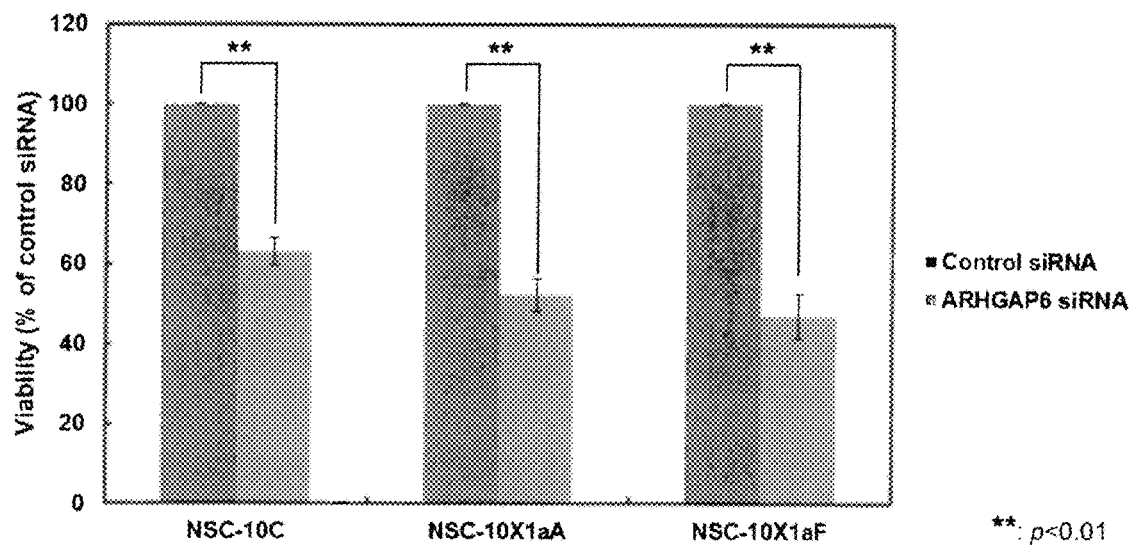
FIG. 2 shows the change in the number of viable cells in the stomach cancer cell line caused by the ARHGAP6 siRNA treatment.

Consequently, the viability of cells decreased (FIG. 2) when the exression level of RP2-ARHGAP6 fusion protein was suppressed by transfecting siRNA that targets ARHGAP6 into all cell lines that endogenously express RP2-ARHGAP6 fusion gene. Since the p value is less than 0.05 even performing the correction by the multiple test method (by Bonferroni method), it was judged that a significant difference exists. It was thus found that suppressing the expression of the fusion gene in the cancer cells that endogenously express the RP2-ARHGAP6 fusion gene has an effect to suppress the growth of cancer cells and/or to decrease the survival of those cells.

Thus, it was found that the RP2-ARHGAP6 defined the tumor advancing capacity of cancer cells.

Example 3 Detection of RP2-ARHGAP6 Fusion Gene

Total RNA prepared from the substrains of NSC-10C, i.e. NSC-10X1A, NSC-10X1aA, NSC-10X1F, NSC-10X1aF, NSC-10X1aX1 and NSC-10X1aX1a, the stomach cancer cell lines KATO-III (JCRB0611, JCRB cell bank) and HSC-39 (provided from National Cancer Center Japan, Animal Experiment Section) and stomach cancer cell lines NSC-9C, NSC-6C and NSC-16C that were established at the Division of Translational Oncology, National Cancer Center Research Institute, in addition to the stomach cancer cell line NSC-10C that expresses an RP2-ARHGAP6 fusion gene shown in Example 1, were reverse-transcribed into cDNA using reverse transcriptase (SuperScriptIII; Life Technologies) and oligo(dT) primer (oligo(dT) 20 primer; Life Technologies).

Figure 3:
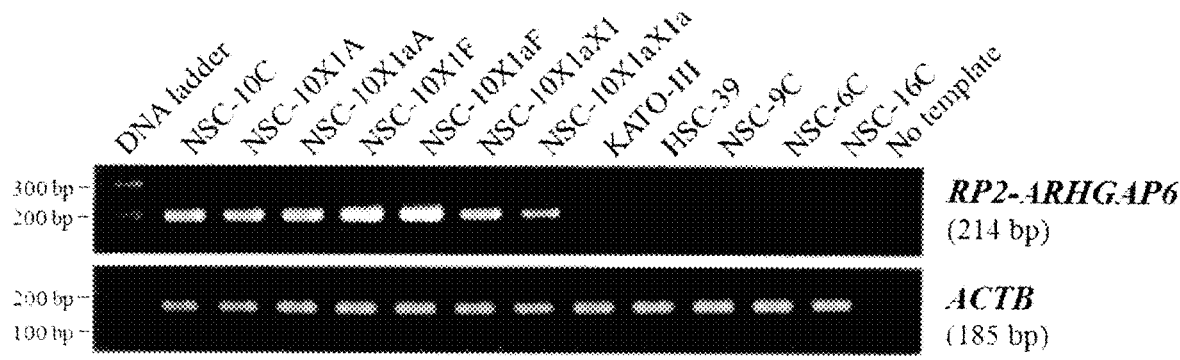
FIG. 3 shows a result of amplification by PCR of a region containing a fusion point of a RP2-ARHGAP6 fusion gene.

Next, primers of RP2_CDS_F23 represented by SEQ ID NO: 7 and ARHGAP6_GCF-R1 represented by SEQ ID NO: 8 were used to perform PCR (2 min. at 94° C., followed by 15 sec. at 94° C., 15 sec. at 55° C., and 1 min. at 68° C., 30 cycles) using DNA polymerase (AccuPrime Taq DNA Polymerase; Life Technologies), and cDNA obtained above as a template (200 ng when converted to total RNA). Likewise, to confirm the equal amount of cDNA template in the reactions, primers of ACTB_F2 represented by SEQ ID NO: 9 and ACTB_R2 represented by SEQ ID NO: 10 were used to perform PCR (2 min. at 94° C., followed by 15 sec. at 94° C., 15 sec. at 55° C., and 1 min. at 68° C., 25 cycles) using the same DNA polymerase as above. Electrophoresis was performed with 2% agarose gel (Lonza) after PCR reaction, and about 200 bp PCR product was amplified only at NSC-10C and substrains thereof which were already confirmed the expression of RP2-ARHGAP6 fusion gene (FIG. 3). The PCR product amplified by the aforementioned primer set was 214 bp according to the nucleotide sequence of the fusion gene identified in Example 1. Therefore, it was showed that the fusion gene that expresses the cancer cells is detectable with PCR method.

INDUSTRIAL APPLICABILITY

The detection method of the present invention is a method for detecting a fusion gene composed of the RP2 gene and the ARHGAP6 gene, and it is useful as a method for detecting and diagnosing cancer in a subject. Further, the primer set and the detection kit of the present invention may be used in a method of the present invention.

The invention claimed is:

1. A method for amplifying a fusion gene composed of part of an retinitis pigmentosa 2 (X-linked recessive) (RP2) gene and part of a Rho GTPase activating protein 26 (ARHGAP26) gene in a sample, wherein the method comprises amplifying a nucleic acid present in the sample with a primer pair consisting of a sense primer consisting of at least 16 consecutive bases between base number 1 to 102 of SEQ ID NO: 1 and an antisense primer consisting of an oligonucleotide complementary to an oligonucleotide of at least 16 consecutive bases between base number 103 to 2439 of SEQ ID NO: 1.

2. The method according to claim 1, wherein the method amplifies portion of a nucleic acid encoding a polypeptide comprising SEQ ID NO: 2, including the fusion portion of the fusion gene.

3. The method according to claim 1, wherein the sample is from a human subject, and the subject is a cancer patient.

4. The method according to claim 3, wherein the subject has stomach cancer.

5. The method according to claim 1, wherein the method amplifies a portion of SEQ ID NO: 1, including the fusion portion of the fusion gene.

* * * * *